United States Patent [19]
Kalb et al.

[11] Patent Number: 5,352,182
[45] Date of Patent: Oct. 4, 1994

[54] PRODUCT AND METHOD TO TREAT FEMALE INCONTINENCE

[76] Inventors: Irvin M. Kalb, 327 Alta Ave., Santa Monica, Calif. 90402; Robert H. Shaw, 243 Peck Dr., Beverly Hills, Calif. 90212; Michael J. Ram, 1 Horseshoe Rd., Bell Canyon, Calif. 91307

[21] Appl. No.: 888,597

[22] Filed: May 27, 1992

[51] Int. Cl.⁵ .................................. A61F 2/02
[52] U.S. Cl. ........................... 600/30; 604/55; 604/93; 604/247; 606/193
[58] Field of Search ............. 604/55, 93, 96-104, 604/105, 106, 246, 247, 329-330; 606/191, 192, 193, 194; 600/29-31

[56] References Cited

U.S. PATENT DOCUMENTS

| | | | |
|---|---|---|---|
| 988,120 | 3/1911 | Lott | 604/104 |
| 1,863,057 | 6/1932 | Innes | 604/105 |
| 2,687,731 | 8/1954 | Iarussi et al. | |
| 3,312,215 | 4/1967 | Silber | 604/104 |
| 3,344,791 | 10/1967 | Fodrick | 604/104 |
| 3,397,699 | 8/1968 | Kohl | 604/105 |
| 3,503,400 | 3/1970 | Osthagen et al. | |
| 3,642,004 | 2/1972 | Osthagen et al. | |
| 3,797,478 | 3/1974 | Walsh et al. | |
| 4,344,434 | 8/1982 | Robertson | |
| 4,453,536 | 6/1984 | Abild | 600/30 |
| 4,489,732 | 12/1984 | Hasson | 128/778 |
| 4,553,959 | 11/1985 | Hickey et al. | |
| 4,571,241 | 2/1986 | Christopher | |
| 4,710,169 | 12/1987 | Christopher | 604/104 |
| 4,932,938 | 6/1990 | Goldberg et al. | 604/104 |
| 4,944,732 | 7/1990 | Russo | |
| 4,968,294 | 11/1990 | Salama | |
| 5,030,199 | 7/1991 | Barwick et al. | 600/29 |
| 5,034,009 | 7/1991 | Mouchel | 128/778 |
| 5,041,092 | 8/1991 | Barwick | |
| 5,074,849 | 12/1991 | Sachse | |
| 5,085,650 | 2/1992 | Giglio | |
| 5,088,980 | 2/1992 | Leighton | |
| 5,090,424 | 2/1992 | Simon et al. | |
| 5,114,398 | 5/1992 | Trick et al. | |
| 5,131,906 | 7/1992 | Chen | 604/104 |
| 5,186,180 | 2/1993 | Bellas | 128/778 |
| 5,234,409 | 8/1983 | Goldberg et al. | 600/30 |

Primary Examiner—C. Fred Rosenbaum
Assistant Examiner—Chalin Smith
Attorney, Agent, or Firm—Michael J. Ram

[57] ABSTRACT

A system for controlling drainage of the female bladder comprising a valved catheter, a stylet for placing the catheter in the female urethra, and a spike for opening the valve in the catheter to allow voiding of the contents of the bladder. The system also includes a sizing device for determining the length of the urethra so that the proper fitting catheter is used. The catheter comprises a hollow shaft with a extendable sealing portion on one end for placement through the urethra and a crown on the other end for placement external of the body. The valve may be integral with the shaft or insertable after the catheter is placed in the urethra.

17 Claims, 4 Drawing Sheets

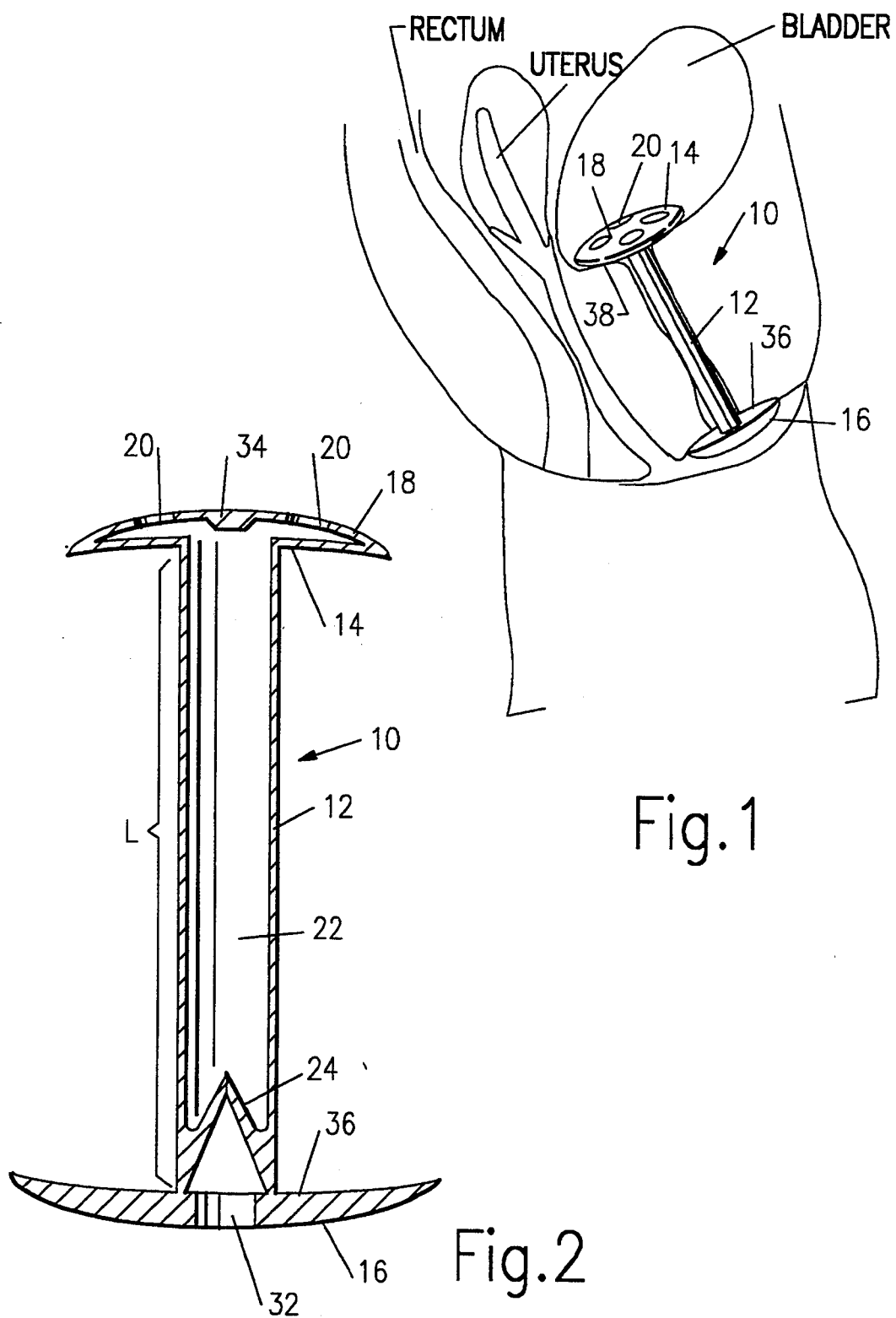

PRODUCT AND METHOD TO TREAT FEMALE INCONTINENCE

BACKGROUND

The present invention relates to a device and a method to control urination in an incontinent female.

A wide spread medical problem suffered by at least 11 million American adults, particularly women is incontinence. Many more suffer from the problem but, because of embarrassment or because the problem is only intermittent,, don't disclose their lack of bladder control. There are numerous causes including pregnancy, stress, as well as the normal aging process.

There presently are no adequate non-surgical techniques for treating this problem. Catheters with an attached bags are uncomfortable and are known to lead to urinary infection. Pads may be effective for small urinary leakage, such as occurs under stress, but are not suitable for large volumes of urine evacuated from a full bladder. Additionally, the use of pads requires the user to carry a large supply of replacement pads. Urethral plugs are unacceptable replacements because the user frequently will soil her hands trying to remove the device, reinsertion of the nonsterile device may lead to a bladder infection and the frequent insertion of the plug, possibly a dozen times a day, can damage the urethra and may cause bladder spasms. Plugs may also be dangerous because they totally obstruct the ureter and may result in excessive retention of urine.

Thus there is a need for a convenient, relatively clean, and frequently repeatable procedure which can be practiced by the woman, and devices which can be used in the procedure. The devices must also be safe to use, discrete, and reliable so that the woman can participate in a normal life style without fear of embarrassing herself by accidentally voiding the contents of her bladder or constantly running to the bathroom to change pads.

SUMMARY

The present invention is directed to a device and method that supplies these needs and eliminates the deficiencies of prior devices and systems.

The device of the invention comprises a valved drainage catheter for temporary placement in the female urethra. Additionally, the system also includes a sizing device for selecting the proper length catheter, a placement device to assure that the catheter is properly positioned and instruments to aid in opening the valve in the catheter.

The catheter comprises a hollow tube with an extendable mushroom head on the internal end, a mushroom shaped cap on the external end and a manually openable valve between the internal end and the external end to prevent urine from exiting the catheter prematurely. The sizing device is of similar shape as the drainage catheter except the catheter has a longer length, the outer surface has measurement indicia spaced along its length and the mushroom cap is replaced by a removable disc shaped similar to the mushroom cap. After insertion of the sizing device in the urethra, the disc is slid along the external portion of the catheter until it rest snugly against the perineal area. The indicia exposed below the disc indicates the correct catheter length for a proper fit.

To place the catheter, the system includes a stylet for insertion into the catheter. Drainage is accomplished by using specially designed valve openers.

DRAWINGS

These and other features, aspects and advantages of the present invention will become better understood with reference to the following description, appended claims, and accompanying drawings, where:

FIG. 1 is a side view showing the drainage catheter placed in the urethra of a female, the female body being shown in cross section.

FIG. 2 is a cutaway side view of the drainage catheter taken along line 2—2 of FIG. 1.

DESCRIPTION

Figure 3A:
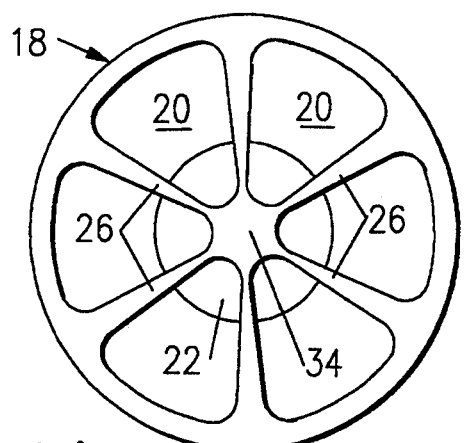
FIG. 3a is a top view of a first embodiment of the internal end of the drainage catheter of FIG. 2.

FIGS. 1 through 4 show a drainage catheter embodying features of the invention.

The drainage catheter 10 includes a tubular center section 12 with a sealing portion on the internal end 14 and a cap 16 on the external end. In the embodiment shown in FIG. 2, the sealing portion is a mushroom shaped crown 18 which can be extended for placement of the catheter. The crown has several drainage holes 20 located in its upper surface. Enclosed in the lumen 22 of the catheter is a one way valve 24 which can be opened by the woman using the catheter 10. In the center of the cap is an drainage outlet 32.

Figure 3B:
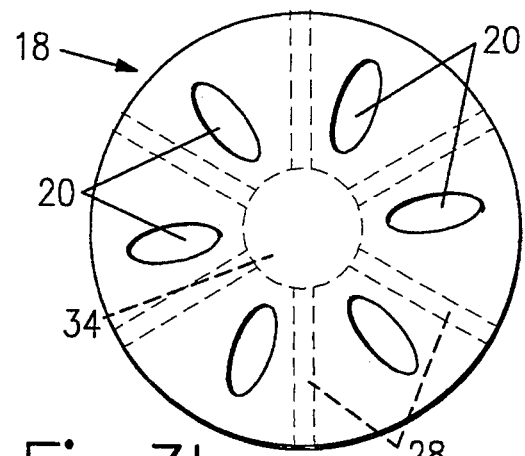
FIG. 3b is a top view of a second embodiment of the internal end of the drainage catheter of FIG. 2.

Alternate designs for the top surface of the crown 18 are shown in FIGS. 3a and 3b. FIG. 3a shows six large drainage holes 20 separated by spokes 26. FIG. 3b shows a similar crown 18 design having smaller holes 20 in the crown surface 28. Shown in phantom in FIG. 3b are struts which depend from the lower or inner surface of the crown 18 to assure that drainage through the holes 20 and into the lumen 22 is not blocked.

Figure 4:
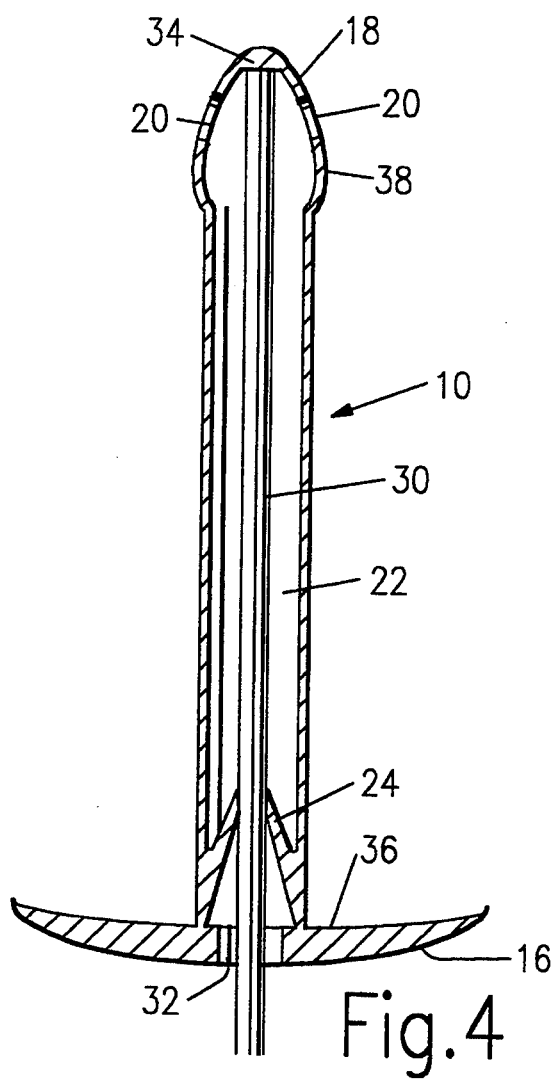
FIG. 4 is a cutaway side view of the drainage catheter taken along line 2—2 of FIG. 1, the catheter being extended for placement.
Figure 7:
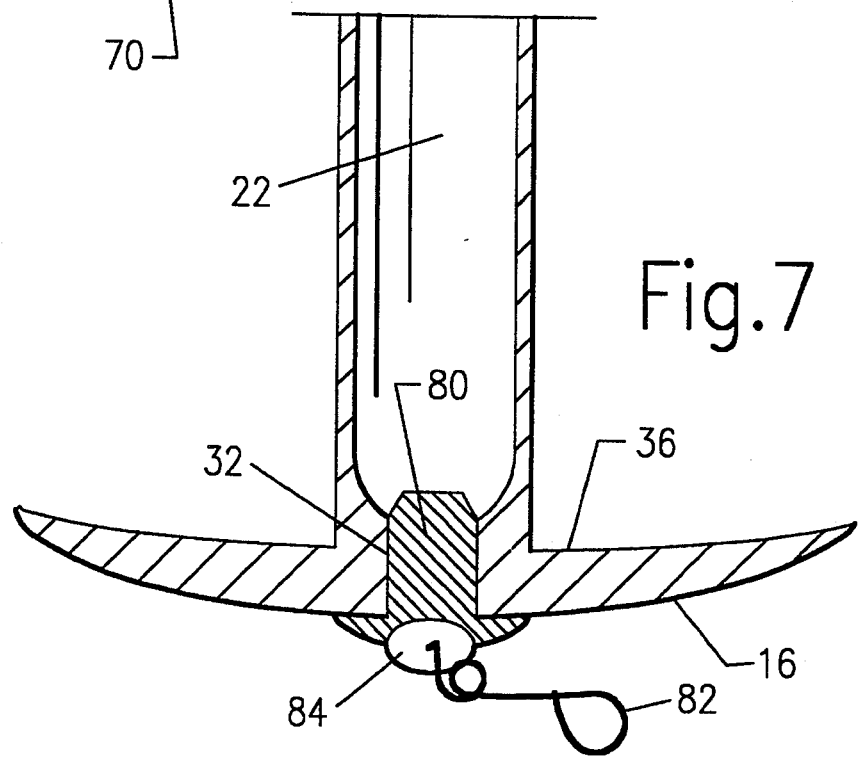
FIG. 7 is an enlarged cutaway side view of the valve section of the drainage catheter of FIG. 2 showing an alternative construction with a plug inserted.
Figure 8A:
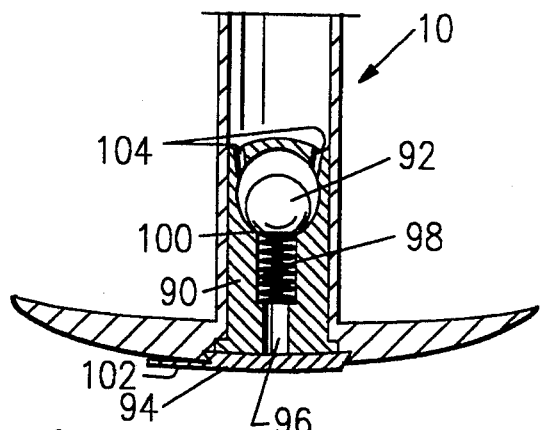
FIG. 8a is an enlarged cutaway side view of the valve section of the drainage catheter of FIG. 2 showing an alternative construction with a magnetic ball valve inserted, the valve being in its closed position.
Figure 8B:
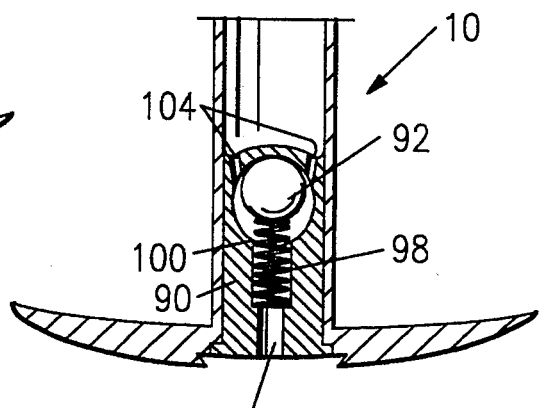
FIG. 8b is an enlarged cutaway side view of the alternative valve section of FIG. 8a in its open position.

The valve 24 shown in FIGS. 2 and 4 is of a duck bill design which prevents fluid from descending down the tube unless the valve is purposefully opened. FIGS. 7, 8a and 8b show two alternative valve structures which will be discussed below.

To insert the catheter 10 into the female ureter a stylet 30 is inserted through the drainage outlet 32 and valve 24 until it comes in contact with the reinforced center 34 of the crown 18. The stylet 30 is then advanced further extending the crown 18 until the diameter of the outer surface of the crown is about the same as the diameter of the catheter 10. The extended crown 18 is then inserted through the external opening of the ureter and advanced until it enters the bladder. If the catheter is properly sized, the inner surface 36 of the cap 16 should be resting snugly against the skin surrounding the external opening of the ureter. Insertion of the catheter 10 may be assisted by applying a small amount of a sterile lubricant to the crown 18. The stylet 30 is then removed while the cap 16 is held in place. Removal of the stylet 30 allows the crown 18 to return to its normal shape with the crown inner surface 38 resting against the bladder surface as shown in FIG. 1.

Figure 5:
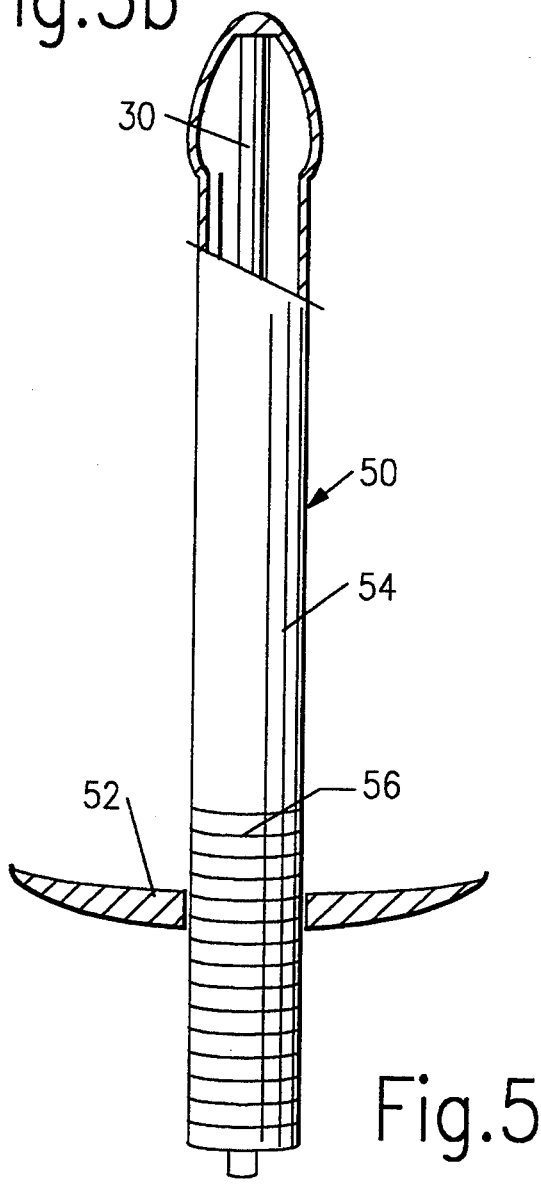
FIG. 5 is partial cutaway view of a sizing device.

In order to minimize or eliminate leakage around the catheter 10 the length L from the crown inner surface 38 to the cap inner surface 36 should be accurately determined. To do so the sizing device 50, shown in FIG. 5, is used. The sizer 50 is of substantially the same shape and has the same outer dimensions as the catheter 10 with the exception that the sizer is longer in length than the catheter 10. However, in place of the cap 16 the sizer 50 has a removable disk 52 which can slide along the outer surface of the sizer tube 54. At least a portion of the tube outer surface has indicia 56 thereon for use in selecting the proper catheter length L. Using the stylet 30 the sizer 50 is inserted into the ureter and the crown is allowed to prolapse against the bladder neck. The disc 52 is then slid along the sizer outer surface until it rests snugly against the tissue surrounding the ureter and the measurement marked on the outer surface of the tube 54 is read. The measurement indicates the catheter size to use for proper fit.

Figure 6:
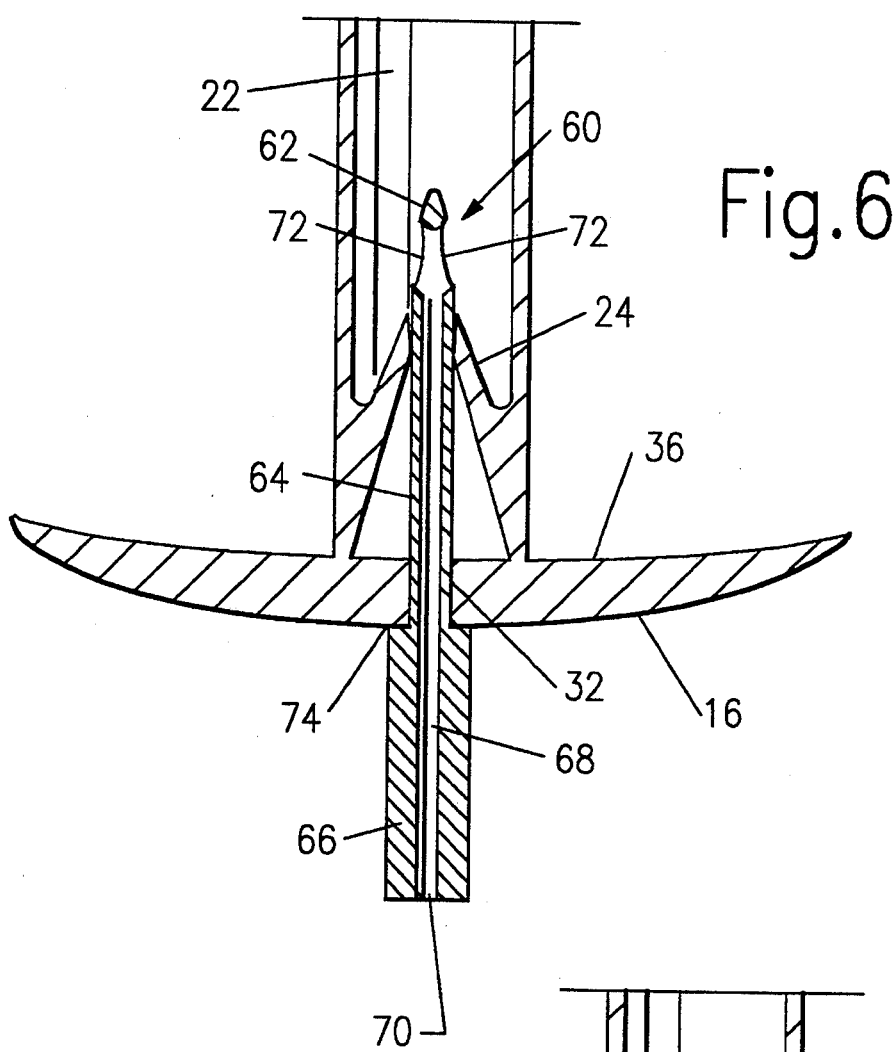
FIG. 6 is an enlarged cutaway side view of the valve section of the drainage catheter of FIG. 2 with a drainage straw inserted.

FIG. 6 shows the valve section of the catheter of FIG. 2 greatly enlarged to show the functioning of the valve during a drainage procedure. To drain the bladder a sterile spike 60 is inserted through the drainage outlet 32 in the external end of the implanted catheter 10. The spike 60 has a center portion 64 sized to fit snugly in the drainage outlet 32 and to open the valve 24. The spike 60 has a tapered head 62 on the top end of the tubular center portion 64 and an enlarged diameter handle 66 on the lower portion. Ports 72 are located at the juncture of the head 62 with the central portion 64. A central lumen 68 starts at the ports 72 and runs the length of the spike 60 terminating in an opening 70 at the base of the handle 66. While the diameter of the central portion 64 is sized to fit snugly through the drainage port 32, the handle diameter is chosen so that it will not easily enter the drainage port 32, thus preventing the head 62 of the spike from being inserted to far into the catheter 10 and damaging the crown 18 or the bladder. Additionally, the combined length of the head 62 and the central portion 64 is chosen so that when the top end 74 of the handle 66 rests against the drainage opening 32, the head 62 pierces the drainage outlet 32 and the valve 24, exposing the ports 70 to a standing column of urine in the catheter 10 above the valve 24. This cooperation of parts allows the user to drainage the bladder without soiling her hands from leaking urine. Once drainage is complete the spike is withdrawn and the valve closes and seals. The spike can then be disposed of or resterilized.

FIG. 7 shows and alternate valve mechanism comprising a plug 80 sized to fit in the drainage opening 32. The plug can be used in place of the valve 24 (as shown in FIG. 7) or in combination with the valve 24 as additional protection against leakage (not shown). The plug is shown with a draw string 82 and a pull tab 84.

FIGS. 8a and 8b shows the catheter 10 with a ball valve mechanism 90 inserted in the external end of a drainage catheter 10. The catheter 10 is shown to have a uniform inner diameter along it entire length. After insertion of the catheter 10 using the stylet 30 and removal of the stylet the ball valve 90 is placed and secured in the catheter 10. The ball valve 90 comprises a ball 92 which is attracted by a magnetic disc 94 placed over the drainage outlet 96. Also enclosed in the valve 90 is a spring 98 which lifts the ball 92 off the seat 100 when the magnetic disc 94 is removed. To raise the ball 92 off the seat 100 the tab 102 is grasped and pulled downward. The removal of the magnetic force allows the spring to lift the ball 92 unsealing the drainage outlet 96 so that the urine can flow through the valve openings 104 and out the catheter 10.

Figure 9A:
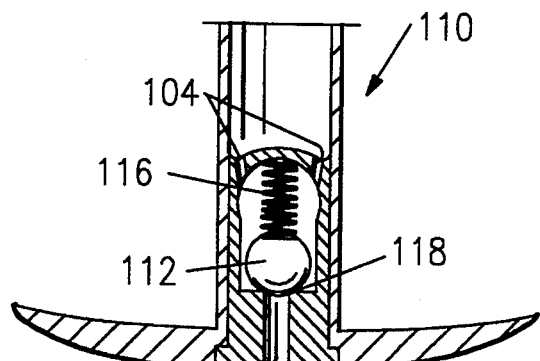
FIG. 9a is an enlarged cutaway view of the valve section of the drainage catheter of FIG. 2 showing a second alternative ball valve structure in its closed structure.
Figure 9B:
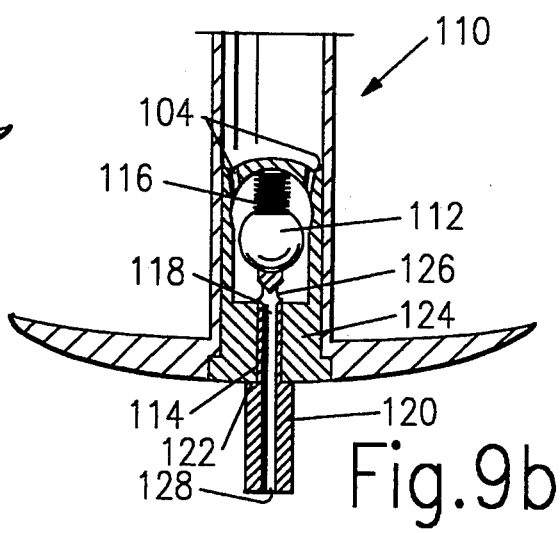
FIG. 9b is an enlarged cutaway side view of the second alternative valve section of FIG. 9b in its open position.

FIGS. 9a and 9b shows the catheter 10 with a ball valve mechanism 110 inserted in the external end of a drainage catheter 10. Like the embodiment shown in FIGS. 8a and 8b, the catheter is also shown to have a uniform inner diameter along its entire length. The valve mechanism 110 is inserted into the catheter 10 after its placement in the urethra. The ball valve 110 comprises a ball 112 which is held against the drainage opening 114 by the spring 116. To raise the ball 112 off the seat 118 a spike 120 is inserted through the drainage opening 114 until the shoulder 122 contacts the bottom 124 of the valve, compressing the spring 116 allowing urine to flow through the valve 110, ports 126 and drainage channel 128 through the center of the spike 120.

The catheter 19 can be fabricated from a broad range of materials presently used for forming urinary catheter including, but not limited to natural and synthetic rubbers, silicone rubbers, thermoplastic elastomers, latex, polyvinyl chloride, polyethylene, and PTFE with or without coatings such as silicone materials, Teflon, hydrophilic compounds and other materials which improve the compatibility with mucosal tissue. Additionally, antibacterials, antiinflammatory drugs, antibiotics or other drugs can be coated on the catheter surface or absorbed into the coatings on the catheter surface. In the embodiment of FIGS. 8a and 8b, the ball 92 is a magnetic material, preferentially a plastic material having magnetic materials or magnetizable materials dispersed therein or ceramometallic materials. The spike 66 or 120 may be formed from a broad range of materials. Stiffness during use is the primary design criteria. Secondly, since the spike is intended to be disposable, the material should be inexpensive. While materials like polyethylene or polypropylene are suitable, a particularly preferred material is a material slowly dissolvable in water or biodegradable so that the spike can be disposed of into the toilet without clogging the plumbing system.

The dimensions of the catheter are dependent on the dimensions of the anatomy of the patient into which the catheter is being placed. The outer diameter of the tubular section 12 of the catheter is about 8 mm and the effective length between the cap 16 and the crown 18 is between about 2.5 and 4.5 cm. However, as indicated, the dimensions can be selected to create a non-leak seal with the patients urinary tract. The diameter of the cap and the crown is from about 12 to 17 mm.

The present invention has been described in considerable detail with reference to certain preferred versions and uses thereof, other versions and uses are possible. Other valves designs, dimensions, materials or crown designs may be used without changing the inventive concept. Therefore, the scope of the appended claims should not be limited to the description of the preferred versions contained herein.

What is claimed is:

1. A urinary drainage catheter for placement in the female urethra, the urethra having an exterior opening at the point of exit from the body and an interior opening at the point of entry into the urinary bladder, the catheter comprising a hollow shaft, a sealing portion on a first end of the shaft and a cap on a second end of the shaft, wherein:

the shaft has a length sized to approximate the length of the urethra and an outer diameter approximating the diameter of the urethra such that the shaft does not extend beyond the exterior opening of the urethra, the sealing portion having
  a) an upper surface with openings therein so that fluid in the bladder can enter the shaft, and
  b) a width greater than the outer diameter of the shaft, the width of the sealing portion being reducible so that the sealing portion can be readily passed through the urethra, a lower surface of said sealing portion resting against the interior end of the urethra, and the cap having a width greater than the outer diameter of the shaft, an upper surface of said cap resting against the exterior opening of the urethra, no portion of the urinary drainage catheter extending exterior of the urethra cap.

2. The urinary drainage catheter of claim 1 further including a valve within the hollow shaft to control flow of fluid through the catheter.

3. A urinary drainage control system comprising a valved urinary drainage catheter for placement in the female urethra, the urethra having an exterior opening at the point of exit from the body and an interior opening at the point of entry into the urinary bladder, a stylet for use in placing the catheter, and a hollow spike for opening the valve to allow drainage of fluid from the bladder, the catheter comprising a hollow shaft with a lumen longitudinally through its center, a sealing portion on a first end of the shaft, a cap on a second end of the shaft, no portion of the urinary drainage catheter extending exterior of the urethra beyond the cap, and a valve located within the lumen of the shaft, wherein:

the shaft has a length sized to approximate the length of the urethra and an outer diameter approximating the diameter of the urethra such that the second end of the shaft is located at the exterior opening of the urethra, the sealing portion has a width greater than the outer diameter of the shaft, there being openings through the sealing portion so that fluid in the bladder can enter the shaft lumen, the width of the sealing portion being reducible so that the sealing portion can be readily passed through the urethra, the cap has a hole therethrough in line with the lumen through the shaft and a width greater than the outer diameter of the shaft, the stylet is a stiff rod with a diameter less than the inner diameter of the shaft and a length greater than the length of the catheter such that insertion of the stylet through the lumen of the catheter and pushing the stylet against the sealing portion causes the sealing portion to elongate and the width to reduce to a diameter suitable for passing through the urethra, the spike having an insertion portion, an exterior portion, a flange on an outer surface thereof separating the insertion portion from the exterior portion, a diameter approximating the inner diameter of the shaft and a length sufficient to enter the valve, the exterior portion of the spike being sized for grasping in the fingers of a user such that when the insertion portion is passed through the hole in the cap and the flange is in contact with the cap the valve opens allowing fluid to drain from the bladder through the shaft, valve and the lumen of the spike without soiling the fingers of the user.

4. A female urethra sizing device comprising a hollow shaft, a sealing portion on a first end of the shaft, a removable disk on a second end of the shaft, and indicia on the outer surface of the shaft, wherein:

the shaft has a length longer than the length of the urethra being measured and an outer diameter approximating the diameter of the urethra, the indicia being located at least on the shaft surface which extends from the urethra when the sealing means is placed in the bladder and against the urethral opening into the bladder, the sealing portion has a width greater than the diameter of the shaft, the width of the sealing portion being reducible so that the sealing portion can be readily passed through the urethra, and the disk is slidable over the shaft outer surface into contact with exterior opening of the urethra after the shaft is placed in the urethra with the sealing means in the bladder, the indicia being observable after the disk is so positioned.

5. The process of placing a fluid drainage control catheter in the female urethra comprising:

determining the diameter and length of the female urethra, placing a catheter in the urethra, the catheter comprising:
  a hollow shaft of an outer diameter approximating the diameter of the urethra, the shaft having a sealing portion on a first end and a cap on a second end, the distance between a lower surface of the sealing portion and an upper surface of the cap approximating the determined length of the urethra and a valve portion located between the first end and the second end, the placement procedure comprising:
  inserting a stylet through a hole in the cap and along the length of the lumen in the shaft into contact with an inner surface on the sealing portion,
  further inserting the stylet along the length of the lumen causing the inner surface of the sealing portion to be temporarily distended from the juncture of the sealing portion with the shaft and temporarily reducing the outer diameter of the sealing portion to a diameter approximating the diameter of the urethra, inserting the distended sealing portion followed by the shaft into the external opening of the urethra and along the length of the urethra until the sealing portion is in the bladder and the cap rests against the exterior opening of the urethra, and removing the stylet from the catheter allowing the sealing portion to resume its original configuration.

6. The process of claim 5 wherein the valve portion of the catheter includes an integral valve located in the lumen of the shaft, the valve being formed so that the stylet can be inserted along the shaft without damaging the valve.

7. The process of claim 5 further including the insertion of a valve into the valve portion of the shaft lumen after removal of the stylet.

8. The process of draining the bladder of a female after insertion of a valved drainage catheter into the female urethra, the catheter comprising a hollow shaft with an inner diameter and an outer diameter, the shaft having a sealing portion on a first end, the sealing portion being located in the female bladder, a cap on a second end of the shaft, the cap being located at the exterior end of the female urethra, and a valve located in the shaft between the sealing portion and the cap, drainage being accomplished by the use of a hollow spike having an insertion portion and an exterior portion, the process comprising:

placing the insertion portion of the hollow spike through an opening in the cap and partially along the length of the hollow shaft into contact with the valve, so that the contact of the spike with the valve causes the valve to open, allowing drainage of fluid from the bladder, through the hollow shaft, the valve and the hollow spike, the insertion portion of the spike having an effective length sufficient only to open the valve and an outer diameter which restricts flow of fluid between the spike outer surface and the shaft inner diameter, the length of the exterior portion of the spike being sufficient for grasping by a user during the drainage procedure, drainage being accomplished without soiling the hands of the user.

9. The urinary drainage catheter of claim 1 wherein the length of the shaft is from about 2.5 cm to about 4.5 cm.

10. The urinary drainage catheter of claim 1 wherein the diameter of the cap and the crown is from about 12 mm to about 17 mm.

11. The urinary drainage catheter of claim 1 wherein the width of the sealing portion can be temporarily reduced to a width approximately the outer diameter of the shaft for passage of the sealing portion readily through the urethra.

12. The urinary drainage catheter of claim 1 where the sealing portion has a crown spaced from the shaft and wherein the width of the sealing portion is reduced to about the outer diameter of the shaft by passing a stylet through the hollow shaft into contact with the crown and moving the crown longitudinally away from the shaft by advancing the stylet further along the length of the shaft.

13. The urinary drainage catheter of claim 2 wherein the valve is openable by inserting a spike having a central lumen through the cap and into contact with a resealable portion of the valve.

14. The urinary drainage catheter of claim 13 wherein the valve is a duck bill valve and the spike opens the valve by passing through the center of the valve allowing urine to flow through the lumen in the spike.

15. The urinary drainage catheter of claim 13 wherein the spike depresses the sealing portion of a spring loaded valve allowing urine to pass through the valve and the lumen in the spike.

16. The urinary drainage catheter of claim 1 wherein urine flow is controlled by a plug inserted into a drainage opening in the cap.

17. The urinary drainage catheter of claim 1 wherein the cap is adapted to receive a valve mechanism which is inserted therein after placement of the catheter in the female urethra.

* * * * *